(12) United States Patent
Brieva et al.

(10) Patent No.: US 6,274,152 B1
(45) Date of Patent: Aug. 14, 2001

(54) COSMETIC COMPOSITIONS

(75) Inventors: Hernando Brieva, Manalapan; Julio Gans Russ, Westfield; Ida Marie Sandewicz, Spotswood, all of NJ (US)

(73) Assignee: Revlon Consumer Products Corporation, New York, NY (US)

( * ) Notice: Subject to any disclaimer, the term of this patent is extended or adjusted under 35 U.S.C. 154(b) by 0 days.

(21) Appl. No.: 09/544,095

(22) Filed: Apr. 6, 2000

Related U.S. Application Data

(63) Continuation of application No. 09/334,844, filed on Jun. 16, 1999, which is a continuation of application No. 08/933,807, filed on Sep. 19, 1997, now Pat. No. 5,965,112, which is a division of application No. 08/599,400, filed on Jan. 5, 1996, now Pat. No. 5,800,816, which is a continuation of application No. 08/328,992, filed on Oct. 25, 1994, now abandoned.

(51) Int. Cl.$^7$ .............................. A61K 6/00; A61K 7/00; A61K 7/021; A61K 7/025; A61K 7/035

(52) U.S. Cl. ..................... 424/401; 424/400; 424/63; 424/64; 424/69

(58) Field of Search ..................... 424/400, 401, 424/63, 64, 69

(56) References Cited

U.S. PATENT DOCUMENTS 5,800,816 * 9/1998 Brieva et al. ..................... 424/63

* cited by examiner

*Primary Examiner*—Thurman K. Page
*Assistant Examiner*—S. Howard
(74) *Attorney, Agent, or Firm*—Julie Blackburn

(57) ABSTRACT

A cosmetic composition having improved transfer resistance comprising:
  a) from about 0.1–60% by weight of trimethylated silica,
  b) from about 0.1–60% by weight of a volatile solvent having a viscosity of 0.5 to 100 centipoise at 25° C.,
  c) 0.1–60% by weight of a nonvolatile oil having a viscosity of 200 to 1,000,000 centipoise at 25° C.
  d) 0.1–80% of a cosmetically acceptable carrier.

17 Claims, No Drawings

COSMETIC COMPOSITIONS

This application is a continuation of Ser. No. 09/334,844, filed Jun. 16, 1999; which is a continuation of Ser. No. 08/933,807, filed Sep. 19, 1997 (now U.S. Pat. No. 5,965,112), which is a divisional of Ser. No. 08/599,400, filed Jan. 5, 1996 (now U.S. Pat. No. 5,800,816), which is a continuation of Ser. No. 08/328,992, filed Oct. 25, 1994 abandoned.

TECHNICAL FIELD

The invention is in the field of cosmetic compositions applied to the skin or hair.

BACKGROUND OF THE INVENTION

Cosmetic compositions are generally defined as compositions suitable for application to the human body. Cosmetic compositions such as creams and lotions are used to moisturize the skin and keep it in a smooth supple condition. Pigmented cosmetic compositions such as makeup, blush, lipstick, and eyeshadow, are used to color the skin and lips. Since color is one of the most important reasons for wearing cosmetics, color containing cosmetics must be very carefully formulated to provide maximum wear and effect.

One of the long standing problems with makeups such as face makeup, lipstick, mascara, and the like, is the tendency of the cosmetic to blot or transfer from the skin or Lashes onto other surfaces such as glassware, silverware, or clothing. This not only creates soiling, but forces the cosmetic user to reapply cosmetic at fairly short intervals. For example, traditional makeup compositions are either water and oil emulsions containing pigments, or they can be anhydrous systems containing waxes, oils and pigments. These formulations are applied and blended into the skin to provide color and correct skin topography to provide an even, smooth appearance. The films are simply deposited on the surface of the skin and if touched with fingers the product may transfer or become blotchy and uneven. Perspiration or sebum will break through the film and cause running or smearing. If skin comes into contact with clothing, the clothing may become soiled.

The object of this invention is to formulate a cosmetic with long lasting adherence to skin.

Another object of the invention is to formulate a cosmetic which yields a film which is not disturbed when blotted to remove sebum or perspiration.

Another object of the invention is to formulate a cosmetic which yields a film which does not readily transfer to clothing or utensils.

Another object of the invention is to formulate a cosmetic which yields a film which exhibits reduced permeability to oil and water.

SUMMARY OF THE INVENTION

The invention is directed to a cosmetic composition having improved transfer resistance comprising:

a) from about 0.1–60% by weight of trimeylated silica, b) from about 0.1–60% by weight of a volatile solvent having a viscosity of 0.5 to 100 centipoise at 25° C., and c) 0.1–60% of a nonvolatile oil having a viscosity of 200 to 1,000,000 centipoise at 25° C.

DETAILED DESCRIPTION

The composition of the invention contains 0.1–60%, preferably 0.5–50%, more preferably 1–30% trimethylated silica particles. One type of trimethylated silica in accordance with the invention has an average particle size of 0.5 to 100 millimcrons. The silica particles may be spheroidal or non-spheroidal, generally having a specific surface area of at least 300 m²/g. Preferably the trimethylated silica particles have a trimethylsilyl group density of 0.5 to 10 micromol/m², and more preferably an alkoxy group density of 0.5 to 10 micromol/m² and a silanol group density of 0.5 to 5 micromol/m². It is preferred that the trimethylated silica particles are spherical. Such trimethylated silica particles in combination with volatile silicone are set forth in U.S. Pat. No. 4,983,388 which is hereby incorporated by reference. Another type of trimethylated silica in combination with volatile solvent, which is used in the preferred embodiment of the invention, is a blend purchased from Dow Corning under the tradename Dow 2-0747 or 2-0749 cosmetic fluid which comprises approximately equal parts of a combination of volatile silicones (decamethylcyclopentasiloxane and octamethylcyclotetrasiloxane) and trimethylated silica.

The volatile solvents of the invention generally have a low viscosity ranging from 0.5 to 100, preferably 0.5 to 20, and more preferably 0.5–10 centipoise at 25° C. Volatile solvents suitable in the composition of the invention include-volatile low viscosity silicone fluids such as cyclic silicones having the formula:

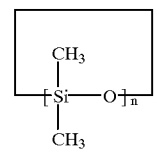

wherein n=1–7. Volatile linear polydimethylsiloxanes are also suitable and generally have from about 2 to 9 silicon atoms and are of the formula:

wherein n=0–7. These silicones are available from various sources including Dow Corning Corporation and General Electric. Dow Corning silicones are sold under the tradenames Dow Corning 244, 245, 344, 345, and 200 fluids. These fluids comprise octamethylcyclotetrasiloxane, decamethylcyclopentasiloxane, hexamethyldisiloxane, or mixtures thereof.

Also suitable as the volatile solvent component are straight or branched chain hydrocarbons having 8–20 carbon atoms, more preferably 10–16 carbon atoms. Suitable hydrocarbons are decane, dodecane, tetradecane, tridecane, and C8-20 isoparaffins as disclosed in U.S. Pat. Nos. 3,439,088 and 3,818,105, both of which are hereby incorporated by reference. Preferred volatile paraffinic hydrocarbons have a molecular weight of 160 to 180 and a boiling point range of 105 to 320 degrees C., a viscosity of less than 20 cs. at 25 degrees C. Such paraffinic hydrocarbons are available from EXXON under the ISOPARS trademark, and Permethyl Corporation. Such $C_{8-20}$ paraffinic hydrocarbons such as $C_{12}$ isoparaffin manufactured by the Permethyl Corporation having the tradename Permethyl 99A™, or a $C_{12}$ isoparaffin (isododecane) are distributed by Presperse having the tradename Permethyl 99A™. Various $C_{16}$ isoparaffins commercially available, such as isohexadecane (having the tradename Permethyl R™) are also suitable. The volatile solvent may be a mixture of volatile silicone and isoparaffins; a ratio of 1:20 to 20:1 respectively is suggested. The volatile solvent preferably ranges from 1–40%, or 5–30% by weight of the total composition.

The nonvolatile oil has a viscosity ranging from 200 to 1,000,000 centipoise at 25° C., preferably 200 to 600,000 centipoise at 25° C., and ranges from 0.1–40%, preferably 0.5–30% by weight of the composition.

The nonvolatile oil may comprise esters of the formula RCO—OR' wherein R and R' are each independently a $C_{1-25}$, preferably a $C_{4-20}$ straight or branched chain alkyl, alkenyl or alkoxy. Examples of such esters include isotridecyl isononanoate, PEG-4 diheptanoate, isostearyl neopentanoate, tridecyl neopentanoate, cetyl octanoate, cetyl palmitate, cetyl ricinoleate, cetyl stearate, cetyl myristate, coco-dicaprylate/caprate, decyl isostearate, isodecyl oleate, isodecyl neopentanoate, isohexyl neopentanoate, octyl palmitate, dioctyl malate, tridecyl octanoate, myristyl myristate, octododecanol tocopheryl acetate, as well as the esters disclosed on pages 24–26 of the *C.T.F.A. Cosmetic Ingredient Handbook*, First Edition, 1988, which is hereby incorporated by reference.

The nonvolatile oil may also comprise high viscosity surface oils generally having a viscosity of 100,000 to 250,000 centipose at 25° C. Such surface oils include castor oil, lanolin, lanolin derivatives, triisocetyl citrate, $C_{10-18}$ triglycerides, caprylic/capric/triglycerides, coconut oil, corn oil, cottonseed oil, hydrogenated castor oil, linseed oil, mink oil, olive oil, palm oil, illipe butter, rapeseed oil, soybean oil, sunflower seed oil, tallow, tricaprin, trihydroxystearin, triisotearin, trilaurin, trilinolein, trimyristin, triolein, tripalmitin, tristearin, walnut oil, wheat germ oil, cholesterol, as well as the oils set forth on pages 26–27 of the *C.T.F.A. Cosmetic Ingredient Handbook*, First Edition, 1988, which is hereby incorporated by reference.

Also suitable as the nonvolatile oil are glyceryl esters and derivatives thereof such as acetylated castor oil, glyceryl stearate, glyceryl dioleate, glyceryl distearate, glyceryl trioctanoate, glyceryl distearate, glyceryl linoleate, glyceryl myristate, glyceryl isostearate, PEG castor oils, PEG glyceryl oleates, PEG glyceryl stearates, PEG glyceryl tallowates, and those further set forth on pages 28–29 of the *C.T.F.A. Cosmetic Ingredient Handbook*, First Edition, 1988. which is hereby incorporated by reference.

Also suitable as the nonvolatile oil are nonvolatile hydrocarbons such as isoparaffins, hydrogenated polyisobutene, mineral oil, squalene, petrolatum, and so on.

Also suitable as the nonvolatile oil are various lanolin derivatives such as acetylated lanolin, acetylated lanolin alcohol, acetylated lanolin ricinoleate, laneth phosphates and acetates, lanolin acid, lanolin linoleate, lanolin wax, PEG hydrogenated lanolins, PEG lanolins, PPG lanolin alcohol ethers, and those further set forth on page 35 of the *C.T.F.A. Cosmetic Ingredient Handbook*, First Edition, 1988, which is hereby incorporated by reference.

Nonvolatile nonfluorinated silicones are also suitable as the nonvolatile component. Such silicones have a viscosity of 200 to 600,000 centistokes, preferably 350 to 100,000 centistokes at 25° C. Suitable silicones include amodimethicone, bisphenylhexamethicone, dimethicone, dimethicone copolyol, dimethiconol, hexadecyl methicone, hexamethyldisiloxane, methicone, phenyl trimethicone, simethicone, dimethylhydrogensiloxane, stearoxy dimethicone, stearoxytrimethylsilane, vinyldimethicone, and mixtures thereof. Such silicones are available from Dow Corning as the 3225C formulation aid, Dow 190 and 193 fluids, or similar products marketed by Goldschmidt under the ABIL tradename.

Also suitable as the nonvolatile oil are various fluorinated oils such as fluorinated silicones or perfluropolyethers. Particularly suitable are fluorosilicones such as trimethylsilyl endcapped fluorosilicone oil, polytrifluoropropylmethylsiloxanes, and similar silicones such as those disclosed in U.S. Pat. No. 5,118,496 which is hereby incorporated by reference. The nonvolatile component may comprise mixtures of fluorosilicones and dimethylpolysiloxanes. The nonvolatile component may also comprise perfluoropolyethers like those disclosed in U.S. Pat. Nos. 5,183,589, 4,803,067, 5,183,588 all of which are hereby incorporated by reference. These perfluoropolyethers are commercially available from Montefluos under the trademark Fomblin.

Other suitable nonvolatile oils include sorbitan derivatives such as PEG sorbitan beeswax, PEG sorbitan isostearate, PEG sorbitan lanolate, PEG sorbitan laurate, PEG sorbitan oleate, PEG sorbitan palmitate, PEG sorbitan stearate, polysorbates, sorbitan trioleates, sorbitan sesquioleates, sorbitan stearates, sorbitan tristearates, and so on, as set forth on page 44 of the *C.T.F.A. Cosmetic Ingredient Handbook*, First Edition, 1988, which is hereby incorporated by reference.

The compositions of the invention may be a water/oil emulsion, color cosmetics such as blush, liquid or powder makeup, eyeshadow, mascara, concealer, lipstick, and so on.

Creams or lotions are generally water and oil emulsions containing water, humectants, surfactants, preservatives, sunscreens, dry particulate matter, and the like. Generally the ranges of these ingredients are 0.1–80% water, 0.01–10% humectants, 0.01–5% surfactants, 0.001–5% preservatives, and 0.001–5% sunscreens. Suitable emollients, humectants, surfactants, preservatives and sunscreens are as set forth in the *C.T.F.A. Cosmetic Ingredient Handbook*, First Edition, 1988, which is hereby incorporated by reference.

Creams may be anhydrous, or aqueous, and water, humectants, surfactants, thickeners, sunscreens, preservatives, and sunscreens, as mentioned above, may also be included.

The creams and lotions of the invention are particularly good vehicles for sunscreen. In particular, about 0.01–10% by weight of various sunscreen compounds such as PABA and derivatives thereof can be incorporated into the cream or lotion. Because the compositions exhibit superior transfer resistance characteristics, the sunscreens are able to remain on the skin for a longer time period. Suitable creams in accordance with the invention are sunscreen creams comprising:

1–30% trimethylated silica
1–40% volatile solvent
0.5–30% nonvolatile oil
0.1–70% dry particulate matter.

The dry particulate matter is largely titanium dioxide and other powdered materials which provide good sunscreen protection.

Preferably, the composition of the invention is incorporated into a vehicle which is a color cosmetic composition such as lipstick, powder, blush, eyeshadow, liquid or powder makeup, and the like.

Suitable face powders generally contain a dry particulate matter have a particle size of 0.02 to 200, preferably 0.5 to 100 microns. The particulate matter may be colored or non-colored (for example white). Suitable powders include bismuth oxychloride, titanated mica, fumed silica, spherical silica, polymethylmethacrylate, micronized teflon, boron nitride, acrylate polymers, aluminum silicate, aluminum starch octenylsuccinate, bentonite, calcium silicate, cellulose, chalk, corn starch, diatomaceous earth, fuller's earth, glyceryl starch, hectorite, hydrated silica, kaolin, magnesium aluminum silicate, magnesium carbonate, magnesium hydroxide, magnesium oxide, magnesium silicate, magnesium trisilicate, maltodextrin, montmorillonite, microcrystalline cellulose, rice starch, silica, talc, mica, titanium dioxide, zinc laurate, zinc myristate, zinc neodecanoate, zinc rosinate, zinc stearate, polyethylene, alumina, attapulgite, calcium carbonate, calcium silicate, dextran, kaolin, nylon, silica silylate, silk powder, sericite, soy flour, tin oxide, titanium hydroxide, trimagnesium phosphate, walnut shell powder, or mixtures thereof. The above mentioned powders may be surface treated with lecithin, amino acids, mineral oil, silicone oil, or various other agents either alone or in combination, which coat the powder surface and render the particles hydrophobic in nature.

The powder component may also comprise various organic and inorganic pigments. The organic pigments are generally various aromatic types including azo, indigoid, triphenylmethane, anthraquinone, and xanthine dyes which are designated as D&C and FD&C blues, browns, greens, oranges, reds, yellows, etc. Organic pigments generally consist of insoluble metallic salts of certified color additives, referred to as the Lakes. Inorganic pigments include iron oxides, ultramarine and chromium or chromium hydroxide colors, and mixtures thereof.

Obviously the percentage of pigments used in the powder component will depend upon the type of cosmetic being formulated. Blushes, eyeshadows, lipsticks and similar cosmetics will contain higher percentages of pigment in the powder phase, usually ranging from 5–50% of the total cosmetic composition. Generally the pigment:powder ratio ranges from 1:20 to 20:1.

Preferred face powder compositions comprise:
0.1–60% trimethylated silica,
0.1–60% of a volatile solvent having a viscosity of 0.5 to 100 centipoise at 250° C., and
0.1–60% of a nonvolatile oil having a viscosity of 200 to 1,000,000 centipoise at 25° C., and
0.01–80% of a dry particulate matter.

The composition of the invention may also be incorporated into mascaras which generally comprise film formers, waxes, emulsifiers, and pigment.

Suitable mascara compositions comprise:
0.1–15% trimethylated silica
0.1–40% of a volatile solvent having a viscosity of 0.5 to 350 centipoise at 250° C.,
0.1–10% of a nonvolatile oil,
0.1–30% of a dry particulate mater,
0.1–20% film former,
0.1–30% wax, and
0.1–10% emulsifier.

Preferably, the volatile solvent comprises a mixture of volatile silicone and a volatile hydrocarbon, and the dry particulate matter comprises a combination of pigments and powders.

Suitable waxes have a melting point ranging from 35 to 120 degrees C., and include natural and synthetic waxes such as bayberry wax, beeswax, candelillia wax, carnauba, ceresin, cetyl esters, hydrogenated jojoba oil, hydrogenated jojoba wax, hydrogenated rice bran wax, japan wax, jojoba butter, jojoba oil, jojoba wax, lanolin wax, microcrystalline, mink, montan acid, montan, ouricury, ozokerite, rice bran, shellac, synthetic beeswax, and synthetic wax, etc.

Suitable film formers include acacia gum, cellulose derivatives, guar derivatives and all those set forth on pages 68–69 of the *C.T.F.A. Cosmetic Ingredient Handbook*, First Edition, 1988, which is hereby incorporated by reference.

Suitable emulsifiers or emulsifying agents are as set forth on pages 90 to 94 of the *C.T.F.A. Cosmetic Ingredient Handbook*, First Edition, 1988, which is hereby incorporated by reference.

The composition of the invention may also be incorporated into water and oil emulsion makeup compositions. Makeup generally contains water, and pigment in addition to an oil phase. Suitable cosmetic makeup compositions comprise:
0.1–20% trimethylated silica
0.1–40% of a volatile solvent having a viscosity of 0.5 to 350 centistokes,
0.1–25% of a nonvolatile oil having a viscosity of 350 to 1,000,000 centipoise at 25° C.,
0.1–70% dry particulate matter having a particle size of 0.02 to 100 microns, and
0.1–50% water.

Preferably, the nonvolatile oils are dimethicone and dimethicone copolyol, and the pigment to powder ratio is 1:20 to 20:1.

The cosmetically acceptable vehicle may also be a blush. Preferred are blush compositions comprising:
0.1–20% trimethylated silica,
0.1–30% of a volatile solvent having a viscosity of 0.5 to 100 centipoise at 25° C.,
0.1–25% of a nonvolatile oil having a viscosity of 200 to 1,000,000 centipoise at 25° C.,
0.1–10% water, and
0.1–70% dry particulate matter having a particle size of 0.02 to 100 microns.

In the above composition, it is preferred that the nonvolatile oils are dimethylhydrogen siloxane, dimethicone, dimethiconol, and fluorosilicone.

The cosmetically acceptable vehicle may also be an eyeshadow. Eyeshadows generally contain pigment or powder in addition to waxes and oils. Preferred eyeshadow compositions comprise:
0.1–20% trimethylated silica,
0.1–30% of a volatile solvent having a viscosity of 0.5 to 100 centipoise at 250° C.,
0.1–40% nonvolatile oil,
0.1–60% dry particulate matter having a particle size of 0.02 to 100 microns.

In the above eyeshadow composition, it is preferred that the volatile solvent comprises cyclomethicone and the nonvolatile oil comprises dimethiconol.

The cosmetically acceptable vehicle may also be a concealer, which generally comprises pigment or powder, wax, and other ingredients such as humectants, preservatives, etc. A preferred composition of the invention is a concealer comprising:
0.1–15% trimethylated silica,
0.1–40% of a volatile solvent having a viscosity of 0.5 to 100 centipoise at 25° C.,
0.1–35% of a nonvolatile oil having a viscosity of 350 to 1,000,000 centipoise at 25° C., and
0.1–40% of a dry particulate matter having a particle size of 0.02 to 100 microns.

In this conceal composition it is preferred that the nonvolatile oil comprises fluorinated silicon, dimethylpolysiloxane or mixtures thereof.

The cosmetically acceptable vehicle may be a lipstick. Lipsticks are generally comprised of wax, oil, and pigment. Preferred lipstick compositions comprise:

0.1–60% trimethylated silica,
0.1–60% volatile solvent,
0.1–60% nonvolatile oil,
0.1–80% dry particulate matter,
0.1–40% wax.

Lipstick compositions may additionally contain one or more of preservatives, antioxidants, emulsifiers, thickeners, and so on. The ingredients corresponding to these categories are set forth in the C.T.F.A. Cosmetic Ingredient Handbook, First Edition, 1988, which is hereby incorporated by reference.

The compositions of the invention provide cosmetics which adhere well to the skin and exhibit reduced transfer resistance.

The invention will be further described in connection with the following examples which are set forth for the purpose of illustration only.

EXAMPLE 1

A makeup composition was made as follows:

|   | w/w % |
|---|---|
| 1 Cyclomethicone/dimethicone copolyol | 20.85 |
| 1 Sorbitan sesquioleate | 0.05 |
| 1 Propyl paraben | 0.10 |
| 1 Titanium dioxide/methicone | 8.00 |
| 1 Red iron oxide/methicone | 0.47 |
| 1 Yellow iron oxide/methicone | 1.16 |
| 1 Black iron oxide/methicone | 0.18 |
| 1 Mica/dimethicone | 0.98 |
| 2 Nylon 12/lecithin | 2.00 |
| 2 Boron nitride | 4.00 |
| 3 Cyclomethicone | 1.00 |
| 3 Dimethicone | 1.50 |
| 3 Dow Corning 2-0747 | 15.00 |
| 3 Tribehenin | 2.00 |
| 4 Glyceryl rosinate/C9–11 isoparaffin | 5.00 |
| 5 Water | 30.00 |
| 6 Methyl paraben | 0.20 |
| 6 Trisodium EDTA | 0.20 |
| 6 Butylene glycol | 4.50 |
| 7 SD alcohol 40-B | 3.00 |

The sequence 1 ingredients were milled in the colloid mill, one after the other until no undispersed white or color was present. Then sequence 2 ingredients were milled in until dispersed. In the main beaker, sequence 1 and 2 were charged and heated to 55–60° C. Then sequence 3 ingredients were added. When tribehenin was all melted, the sequence 4 ingredients were added. For the water phase, in a side beaker the sequence 5 ingredients and the pre-mix of sequence 6 were heated to 50–55° C. Right before emulsification, the sequence 7 ingredients were added to the water phase. The water phase and the oil phase were then emulsified using a homogenizer for 15 minutes. The mixture was cooled using a paddle mixer.

EXAMPLE 2

A mascara composition was made as follows:

|   | w/w % |
|---|---|
| Carnauba wax | 4.25 |
| Candelilla wax | 9.25 |
| Beeswax | 4.60 |
| Synthetic wax | 4.85 |
| BHA | 0.05 |
| Propyl paraben | 0.10 |
| Glyceryl rosinate/$C_{9-11}$ isoparaffin | 12.00 |
| Lanolin acid | 6.00 |
| Isododecane | 16.40 |
| Oleyl alcohol | 1.00 |
| Black iron oxide | 10.00 |
| Silica | 4.50 |
| Polyethylene | 2.00 |
| Water | 7.60 |
| Methyl paraben | 0.35 |
| Sodium EDTA | 0.10 |
| Sodium dehydroacetate | 0.30 |
| Yeast glycoprotein | 1.00 |
| Hydrolyzed keratin | 0.05 |
| Ammonium hydroxide | 0.60 |
| Dow Corning 2-0747 | 15.00 |

The ingredients were mixed sequentially.

EXAMPLE 3

A blush on was made as follows:

|   | w/w % |
|---|---|
| Dow Corning 2-0747 cosmetic fluid | 32.50 |
| Dow Corning silastic Q7-4350 (silica, methyl and methyl vinyl siloxane copolymer) | 5.50 |
| Dimethicone/dimethiconol | 3.00 |
| Boron nitride | 5.00 |
| Talc | 4.00 |
| Water | 2.00 |
| Ethyl alcohol | 3.00 |
| Iron oxides | 3.00 |
| Red #30 lake | 1.80 |
| Titanium dioxide | 4.00 |
| Quaternium 18 hectorite/cyclomethicone | 20.00 |
| Cyclomethicone | 12.20 |
| Trifluoropropylmethylpolysiloxane (Dow Corning FS-1265) | 4.00 |

EXAMPLE 4

A concealer was made as follows:

|   | w/w % |
|---|---|
| Dow Corning 2-0747 | 20.00 |
| Iron oxides | 4.00 |
| Titanium dioxide | 14.00 |
| Talc | 8.00 |
| Water | 3.00 |
| Ethyl alcohol | 3.00 |
| Dow Corning Silastic Q7-4350 | 7.00 |
| Dimethyl polysiloxane | 10.00 |
| Cyclomethicone | 19.00 |
| Trifluoropropylmethyl polysiloxane (Dow Corning FS-1265) | 4.00 |

EXAMPLE 5

An eyeshadow formulation was made as follows:

|  | w/w % |
| --- | --- |
| Talc | 22.41 |
| Mica | 20.00 |
| Zinc stearate | 1.50 |
| Polyethylene/talc | 5.00 |
| Mica/titanium dioxide | 10.00 |
| Polyethylene | 1.50 |
| Bismuth oxychloride | 4.49 |
| Titanium dioxide | 4.00 |
| Black iron oxide | 0.15 |
| Yellow iron oxide | 0.35 |
| Red iron oxide | 0.60 |
| Dow Corning 2-0747 | 22.00 |
| Cyclomethicone | 2.00 |
| Cyclomethicone/dimethiconol | 3.00 |
| Coco caprylate caprate | 3.00 |

EXAMPLE 6

A sun-blocking cream was made as follows:

|  | w/w % |
| --- | --- |
| Dow Corning 2-0747 | 30.00 |
| Iron oxides | 3.50 |
| Titanium dioxide | 20.00 |
| Zinc Oxide | 5.00 |
| Boron nitride | 8.00 |
| Dow Corning Silastic Q7-4350 | 7.00 |
| Hexamethyl disiloxane | 10.00 |
| Cyclomethicone | 11.50 |
| Trifluoropropylmethyl polysiloxane | 5.00 |

EXAMPLE 7

The eyeshadow formula of Example 5 was subjected to panel testing. Three panelists were asked to apply the eyeshadow to the eyelids. Fourteen hours later the panelists were asked to rate the eyeshadow as follows:

|  | No. of panelists | |
| --- | --- | --- |
|  | Yes | No |
| Was ES smooth & creamy | 3 | 0 |
| Did ES apply easily | 3 | 0 |
| Did ES have good deposit | 3 | 0 |
| Did ES have even coverage | 3 | 0 |
| Did ES have good appearance | 3 | 0 |
| How long did ES wear: | 12 hours - 2 panelists | |
|  | 10 hours - 1 panelist | |

While the invention has been described in connection with the preferred embodiment, it is not intended to limit the scope of the invention to the particular form set forth, but, on the contrary, it is intended to cover such alternatives, modifications, and equivalents as may be included within the spirit and scope of the invention as defined by the appended claims.

We claim:

1. An anhydrous pigmented composition comprising, by weight of the total composition:
   0.1–20% trimethylated silica,
   1–30% volatile solvent volatile solvent having a viscosity of 0.5 to 20 centipoise at 25° C. selected from the group consisting of a cyclic silicone having the formula:

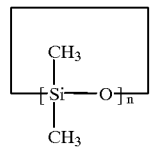

wherein n=1–7; a linear silicone having the formula:

wherein n=0–6; a straight or branched chain hydrocarbon having 8–20 carbon atoms; ethanol; and mixtures thereof;
   0.1–40% nonvolatile oil, and
   0.1–60% particulate matter having a particle size of 0.02 to 100 microns wherein at least a portion of the particulates are surface treated with lecithin.

2. The composition of claim 1 wherein the trimethylated silica has a silanol endgroup density of 0.5 to 5 micromol/$m_2$.

3. The composition of claim 1 wherein the trimethylated silica is in the form of spherical particles.

4. The composition of claim 1 wherein the trimethylated silica has a particle size of 0.5 to 100 millimicrons.

5. The composition of claim 1 wherein the trimethylated silica is found in a cosmetic fluid composition comprising about equal parts of volatile solvent and trimethylated silica.

6. The composition of claim 1 wherein the volatile solvent is an cyclomethicone, a straight or branched chain hydrocarbon having 8–20 carbon atoms, and mixtures thereof.

7. The composition of claim 1 wherein the nonvolatile oil comprises an oil selected from the group consisting of dimethicone, dimethicone copolyol, and mixtures thereof.

8. The composition of claim 1 wherein the nonvolatile oil comprises esters.

9. The composition of claim 8 wherein the nonvolatile oil comprises esters and an oil selected from the group consisting of dimethicone, dimethicone copolyol, and mixtures thereof.

10. The composition of claim 1 wherein the particulate matter comprises, in addition to titanium dioxide, one or more pigments or powders having a particle size of 0.02 to 200 microns.

11. The composition of claim 10 wherein the pigments comprise inorganic pigments, organic pigments, or mixtures thereof.

12. The composition of claim 10 wherein the particulate matter further comprises zinc oxide.

13. The composition of claim 10 wherein the particulate matter further comprises boron nitride.

14. The composition of claim 1 further comprising a wax.

15. The composition of claim 14 wherein the was is polyethylene.

16. The composition of claim 1 which is selected from the group consisting of eyeshadow and blush.

17. An anhydrous pigmented cosmetic composition comprising, by weight of the total composition:
   1–30% trimethylated silica having a silanol endgroup density of 0.5 to 5 micromol/$m^2$,
   1–40% volatile solvent having a viscosity of 0.5 to 20 centipoise at 25° C., selected from the group consisting of a cyclomethicone, hexamethyldisiloxane, isododecane, and mixtures thereof, 05–30% of a nonvolatile oil selected from the group consisting of dimethicone, dimethicone copolyol, and mixtures thereof; and 0.1–70% particulate matter comprising titanium dioxide and an ingredient selected from the group consisting of zinc oxide, boron nitride, silica, mica, iron oxides, and mixtures thereof wherein one or more of the particulates are surface treated with lecithin.

* * * * *